United States Patent [19]

Neusel

[11] 4,081,628
[45] Mar. 28, 1978

[54] MICROPHONE, PARTICULARLY FOR BODY SOUNDS, WITH SLIP COUPLING TO THE TRANSDUCER ELEMENT

[76] Inventor: Rolf Neusel, Hugelstrasse 69, D-6100 Darmstadt, Germany

[21] Appl. No.: 746,325

[22] Filed: Dec. 1, 1976

[30] Foreign Application Priority Data

Dec. 5, 1975 Germany .............................. 2554777

[51] Int. Cl.² .......................... H04R 1/46; H04R 17/02
[52] U.S. Cl. ............................ 179/121 R; 179/110 A; 179/121 C; 179/184
[58] Field of Search ............ 179/1 ST, 110 A, 121 R, 179/121 C, 184

Primary Examiner—George G. Stellar
Attorney, Agent, or Firm—Michael J. Striker

[57] ABSTRACT

A microphone housing includes an electromechanical transducer element. An interior diaphragm is mounted in the housing. A slip coupling connects the interior diaphragm to the transducer element for transmitting forces from the former to the latter. An exterior diaphragm is mounted in the housing and defines together with the interior diaphragm an intermediate coupling space through which vibrations of the exterior diaphragm are transmitted to the interior diaphragm.

6 Claims, 1 Drawing Figure

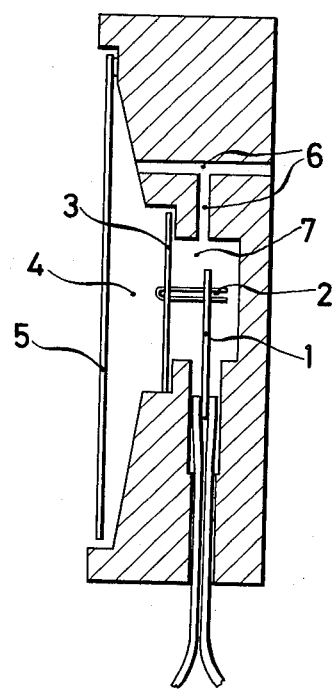

MICROPHONE, PARTICULARLY FOR BODY SOUNDS, WITH SLIP COUPLING TO THE TRANSDUCER ELEMENT

With known microphones, particularly for detecting body sounds, the actual transducer elements, for example piezoelectric elements, are mechanically connected to the diaphragms in such a manner that diaphragm deflections which considerably exceed the safe mechanical operating range of the transducer element produce the danger of destruction of the transducer element, or at least produce the danger of an interfering mechanical pre-stressing of the transducer element. This situation is particularly disadvantageous when blood pressure is to be measured using the Korottkoff sounds.

An exemplary embodiment is depicted in FIGS. 1 and 2.

FIG. 1 is a section through an exemplary embodiment of the inventive microphone, whereas FIG. 2 is a perspective view of the inner diaphragm, the transducer element and the slip coupling of the structure shown in FIG. 1.

Reference numeral 1 denotes an electromechanical transducer element of any conventional type connected by means of a slip coupling 2 to an interior diaphragm 3. Electrical leads 1a, 1b are connected to opposite sides of the transducer element 1, for transmission of the low-level voltage which develops across the transducer element 1 when the latter is flexed. The slip coupling is so dimensioned that, within the permissible operating range of the transducer element 1, no slipping of the coupling occurs; however, if the safe operating range of the transducer element 1 is exceeded, the slip coupling 2 commences to slip thereby protecting the transducer element from damage. By appropriately dimensioning the slip coupling, it is possible to always keep the transducer element within its safe operating range. The interior diaphragm 3 is mechanically coupled with an exterior diaphragm 5 by means of a coupling space 4, so that movements of the exterior diaphragm will be transmitted to the interior diaphragm to a degree dependent upon the coupling characteristics exhibited by coupling space 4. To be able to establish the frequency response and the null setting of the interior diaphragm, there are provided connections from the coupling space 4 to the ambient atmosphere and/or to a space 7 located at that side of interior diaphragm 3 which faces away from exterior diaphragm 5; these connections are denoted by numeral 6 in the FIG. 1. These connections are matched, relying upon known fluid dynamics principles, to the intended use of the microphone. For example, the load on the exterior diaphragm may include a component which changes slowly but over a large range of pressure values; it may be desired that this component of load not be transmitted to the interior membrane and to the transducer element to such an extent as to cause the latter to exceed its safe operating range, while leaving intact the sensitivity of the interior membrane and transducer element to small but quick pressure changes, this being particularly advantageous in the case of blood pressure measurements.

The invention also contemplates being able to freely select the surface area ratio of the exterior diaphragm to the interior diaphragm, in order to achieve integrating and/or step-up action, in accordance with known principles.

The structural components of the microphone can be made of conductive material or of non-conductive material provided with layers of conductive material, in order to prevent electrical interference effects. If an electromagnetic transducer element is employed, then the structural components can be made of a magnetically shielding material. The structural components can be made of a plurality of different materials, as another possibility.

If the interior diaphragm is designed as an electret or as a piezoelectric transducer, then it may be possible to dispense with the slip coupling.

The invention additionally contemplates including impedance converters and/or amplifiers structurally integrated with the microphone as a single unit.

It will be understood that each of the elements described above, or two or more together, may also find a useful application in other types of constructions differing from the types described above.

While the invention has been illustrated and described as embodied in a microphone, particularly adapted for picking up body sounds, it is not intended to be limited to the details shown, since various modifications and structural changes may be made without departing in any way from the spirit of the present invention.

Without further analysis, the foregoing will so fully reveal the gist of the present invention that others, can, by applying current knowledge, readily adapt it for various applications without omitting features that, from the standpoint of prior art, fairly constitute essential characteristics of the generic or specific aspects of this invention.

What is claimed as new and desired to be protected by Letters Patent is set forth in the appended claims.

1. A microphone, particularly for picking up body sounds, underwater sounds and air-transmitted sounds, comprising a microphone housing; an electromechanical transducer element mounted in the housing; an interior diaphragm mounted in the housing; a slip coupling connecting the interior diaphragm to the transducer element for transmitting forces from the former to the latter; an exterior diaphragm mounted in the housing and defining together with the interior diaphragm an intermediate coupling space through which vibrations of the exterior diaphragm are transmitted to the interior diaphragm.

2. The microphone defined in claim 1, the housing including passage means connecting the coupling space to the ambient atmosphere.

3. The microphone defined in claim 1, the housing including passage means connecting the coupling space to the space adjoining that side of the interior diaphragm not facing the coupling space.

4. A microphone defined in claim 1, the housing including passage means connecting the coupling space to the ambient atmosphere and also to the space adjoining that side of the interior diaphragm not facing the coupling space.

5. The microphone defined in claim 1, the microphone housing being comprised of electrically conductive material.

6. The microphone defined in claim 1, the transducer element being a piezoelectric element.

* * * * *